United States Patent [19]

Cho

[11] Patent Number: 5,360,425

[45] Date of Patent: Nov. 1, 1994

[54] SCLEROSTOMY METHOD AND APPARATUS

[75] Inventor: George Cho, Natick, Mass.

[73] Assignee: Candela Laser Corporation, Wayland, Mass.

[21] Appl. No.: 820

[22] Filed: Jan. 5, 1993

Related U.S. Application Data

[63] Continuation of Ser. No. 568,961, Aug. 17, 1990, abandoned.

[51] Int. Cl.$^5$ .............................................. A61N 5/06
[52] U.S. Cl. ........................................ 606/6; 606/16; 606/17
[58] Field of Search ........................................ 606/2–4, 606/6, 7, 13–17; 607/88, 89

[56] References Cited

U.S. PATENT DOCUMENTS 4,669,467 6/1987 Willett et al. ........................... 606/15
4,686,979 8/1987 Gruen et al. ............................. 606/7
4,846,172 7/1989 Berlin ........................................ 606/4
4,963,142 10/1990 Loertscher .............................. 606/14

OTHER PUBLICATIONS

"The Holmium Laser, A new laser for the treatment of glaucoma," Sunrise Technologies Brochure, Sunrise Technologies, Inc., 47257 Fremont Boulevard, Fremont, Calif. 94538.

H. D. Hoskins, Jr. et al., Subconjuctival THC:YAG Laser Limbal Sclerostomy AB Externo In The Rabbit.

Mark Latina, M. D. et al., Laser research: improving surgery's chances for success, Sundial, The Newsletter of the Eye Research Institute of Retina Foundation, vol. 14, No. 2, Spring 1988, pp. 9–10.

Primary Examiner—David M. Shay
Attorney, Agent, or Firm—Testa, Hurwitz & Thibeault

[57] ABSTRACT

A fistula is created in the sclera of a glaucoma patient by creating a passageway through the conjunctiva into the subconjunctival space of the patient. The passageway may be realized by an incision but is preferably realized as the inner lumen of a needle or sheath. One option for creating such an incision is to use an optical fiber shaped like a needle to create the incision. The passageway enables an optical fiber to pass into the subconjunctival space. Liquid is then infused into the subconjunctival space to raise the conjunctiva slightly to heighten maneuverability of the optical fiber within the subconjunctival space. The optical fiber is then positioned near a target sight on the sclera of the patient's eye. Laser radiation is transmitted down the optical fiber to create a fistula.

26 Claims, 9 Drawing Sheets

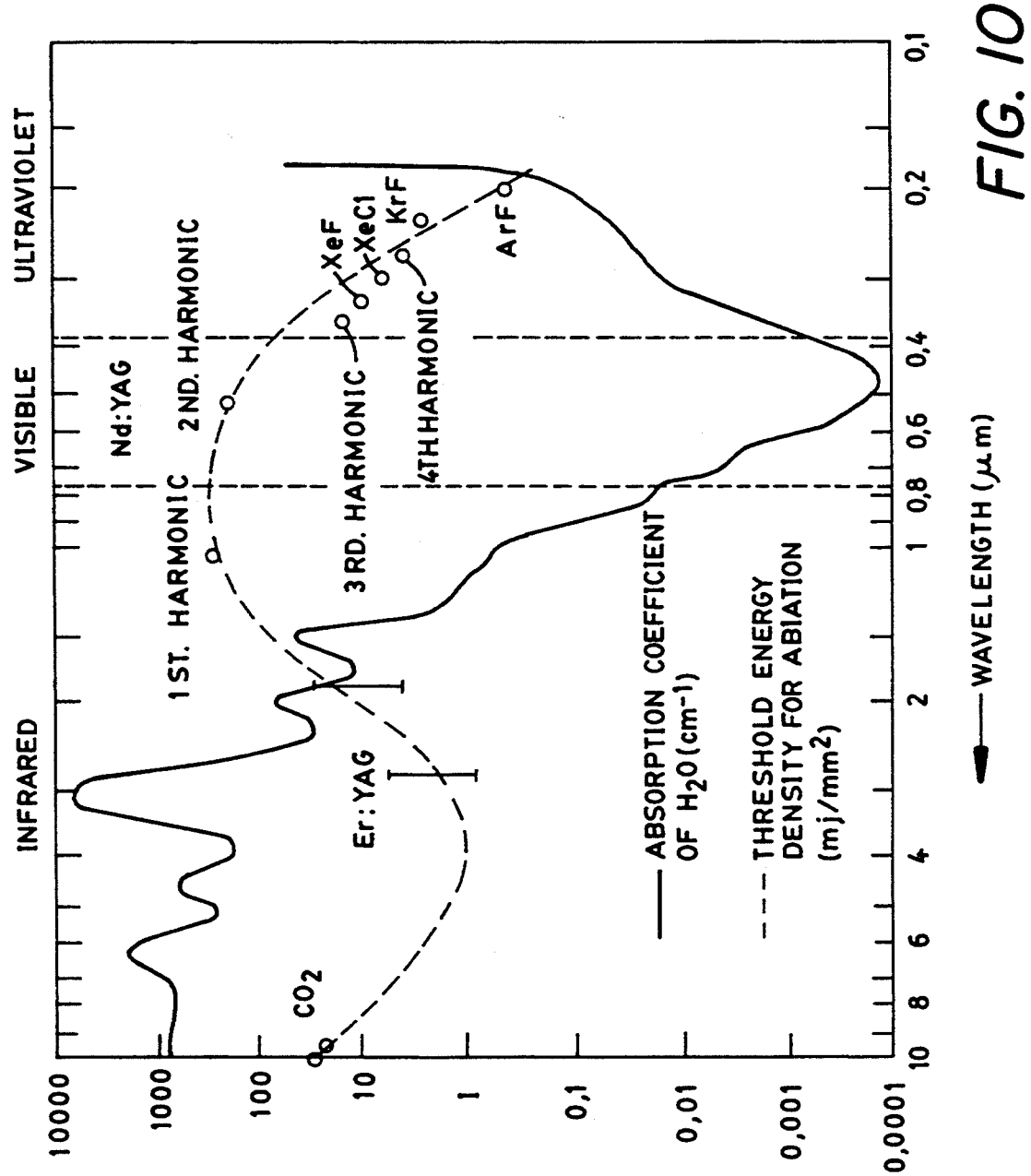

SCLEROSTOMY METHOD AND APPARATUS

This is a continuation of copending application Ser. No. 07/568,961, filed on Aug. 17, 1990, now abandoned.

BACKGROUND OF THE INVENTION

One of the more troubling symptoms suffered by glaucoma patients is a significant increase in intraocular pressure. This increase in pressure may lead to eye damage and even blindness in some patients. One means for relieving the intraocular pressure is to create an alternative outflow channel in the patients eye through a sclerostomy procedure. In that procedure, a fistula is created in the sclera at the peripheral regions of the cornea. The fistula allows liquid aqueous humor produced inside the eye to drain into subconjunctival space and, hence, decrease the volume of liquid contained within the eye. The decrease in volume of liquid results in a corresponding decrease in intraocular pressure. From the subconjunctival space, the liquid is gradually absorbed or translocated away from the interior of the eye. One sclerostomy approach is presented in application Ser. No. 07/356,885 filed by Hsia et al. entitled, "Method and Laser Apparatus for Creating a Fistula in the Sclera of the Eye". That approach involved dyeing a target area so that it would absorb laser energy. Once the area was appropriately dyed, laser energy was directed to reflect off a goniolens through the cornea to the target area.

SUMMARY OF THE INVENTION

The method outlined in pending patent application Ser. No. 07/356,885 requires coupling of a laser through a slit lamp assembly and goniolens. In this method, the laser beam must pass through the cornea and anterior chamber of the eye to reach the target site at the sclera. To perforate the sclera, dyeing of the sclera is required. Dyeing can be performed by an iontophoresis apparatus. The present invention provides an alternative procedure which requires no dyeing and which allows direct application of the laser light to the target site without requiring the light to pass through the cornea and anterior chamber of the eye.

The present invention concerns an ab externo method of performing sclerostomy. In accordance with this method, a passageway is created through the conjunctiva into the subconjunctival space of the eye. The passageway is used to feed an optical fiber into the subconjunctival space. The passageway may be the inner lumen of a needle. Alternatively, the passageway may be the inner lumen of a sheath that surrounds a needle. This sheath is inserted with the needle and, then, the needle is removed while leaving the sheath in place. Lastly, the passageway may be an incision created in the conjunctiva.

To position a needle under the conjunctiva, it should be inserted at an angle under the conjunctiva at a location spaced from the corneo-scleral junction. When a needle is used, the needle preferably is no larger than 26 gauge. Preferably, the needle is 27 gauge. Larger needles leave a larger perforation in the conjunctiva when they are removed from the eye such that conjictava repair may be necessary to prevent fluid leakage.

Once the passageway has been created, an optical fiber or other device for carrying laser radiation is passed through the passageway into the subconjunctival space. To provide extra space and lubrication for the positioning of the optical fiber, it is preferred that the conjunctiva of the eye be raised to form a small bleb by infusing liquid into the subconjunctival space. One approach to injecting the conjunctiva with liquid is to infuse the liquid via the needle that carries the optical fiber.

After the conjunctiva has been slightly raised, the optical fiber is positioned at the target site. Preferably, the optical fiber is positioned in contact with the target site. Laser radiation is then carried down the optical fiber to ablate the sclera of the patient's eye. The optical fiber should have an outer diameter no larger than 350 microns and preferably has an outer diameter of about 100 to 200 microns. The laser radiation preferably has a wavelength in the range of approximately 1.5 to 3.0 microns. It is also preferred that the laser radiation be sent as a series of pulses to the target site. The pulse duration should be in the range of approximately 10 to 225 microseconds. An energy range of 50 to 200 millijoules is preferred. As the sclera is ablated, the optical fiber may be pushed forward to maintain contact between the fistula site and the optical fiber to maintain high ablating efficiency. Moreover, the pushing forward of the optical fiber avoids absorption by surrounding liquid and lessens the need for using laser radiation that is deeply absorbed by the eye tissue.

The needle may be attached to a syringe having a first channel for infusing fluids and a second channel for carrying the optical fiber. The positioning of the first channel relative to the second channel may take different forms. For instance, the second channel may be disposed within the first channel. Alternatively, the second channel may be situated adjacent to the first channel. The two channels feed into to the needle.

BRIEF DESCRIPTION OF THE DRAWING

FIG. 10 is a plot of the absorption curve of water for different wavelengths of light.

DETAILED DESCRIPTION OF THE PREFERRED EMBODIMENT

An alternative outflow channel or fistula is created in the present invention to create a drain for excess aqueous humor in a patient's eye. The drainage of the aqueous humor through the fistula reduces intraocular pressure and thus helps relieve a major difficulty suffered by glaucoma patients.

Figure 1:
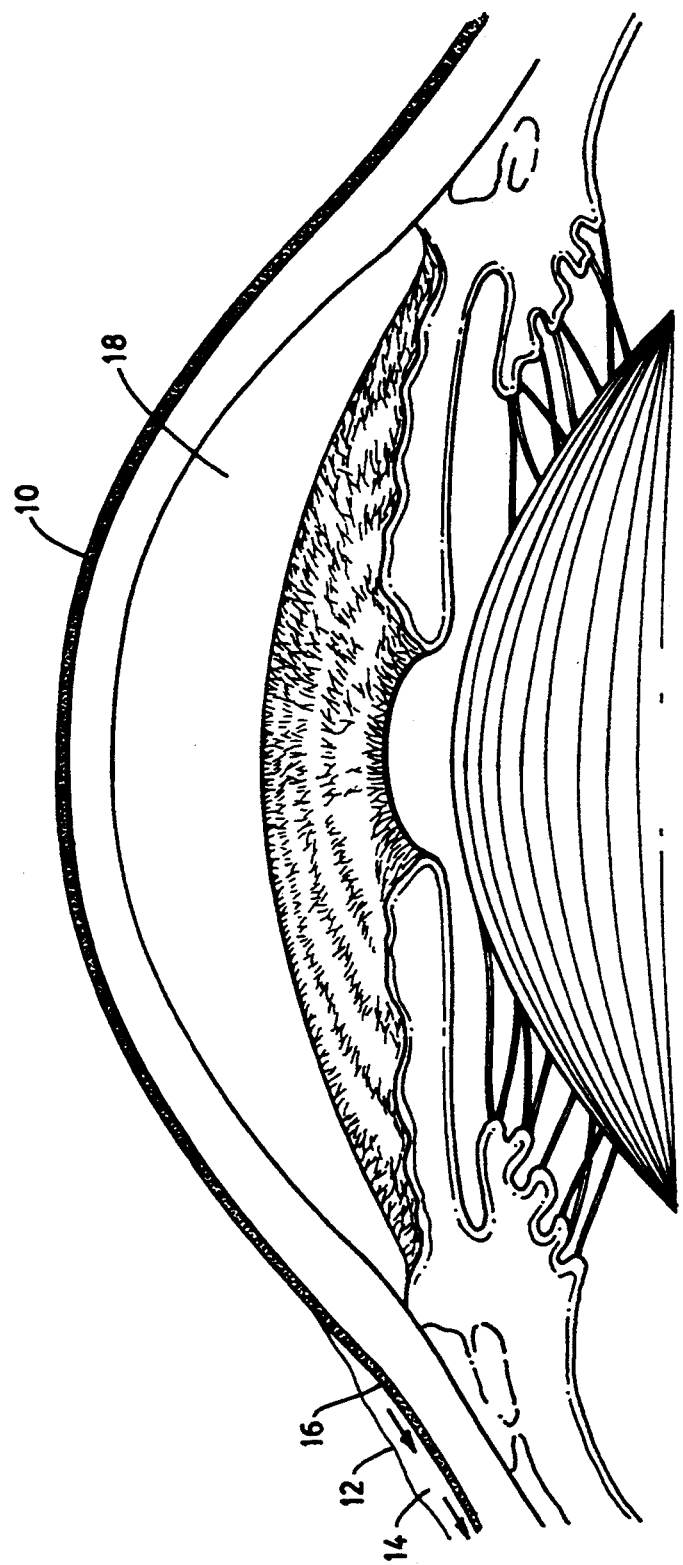
FIG. 1 shows a cross-sectional view of the human eye.

FIG. 1 depicts a cross-sectional view of the human eye. The cornea 10 is a protruding anterior transparent portion of the eye. Situated behind the cornea is the anterior chamber 18. The eye also includes a sclera 16, which is a tough white outer envelope of tissue that covers all of the exterior of the eyeball other than the cornea. The sclera 16 is covered by a conjunctiva 12 at the anterior section. Of particular interest to the present invention are the portions of the eye known as the conjunctiva 12 and the subconjunctival space 14, which is the space located between the conjunctiva 12 and the sclera 16. The conjunctiva 12 is a thin translucent membrane, having a thickness of approximately 20 to 30 microns. The sclera 16, in contrast, is much thicker with a typical thickness of approximately 0.8 millimeters.

Figure 2:
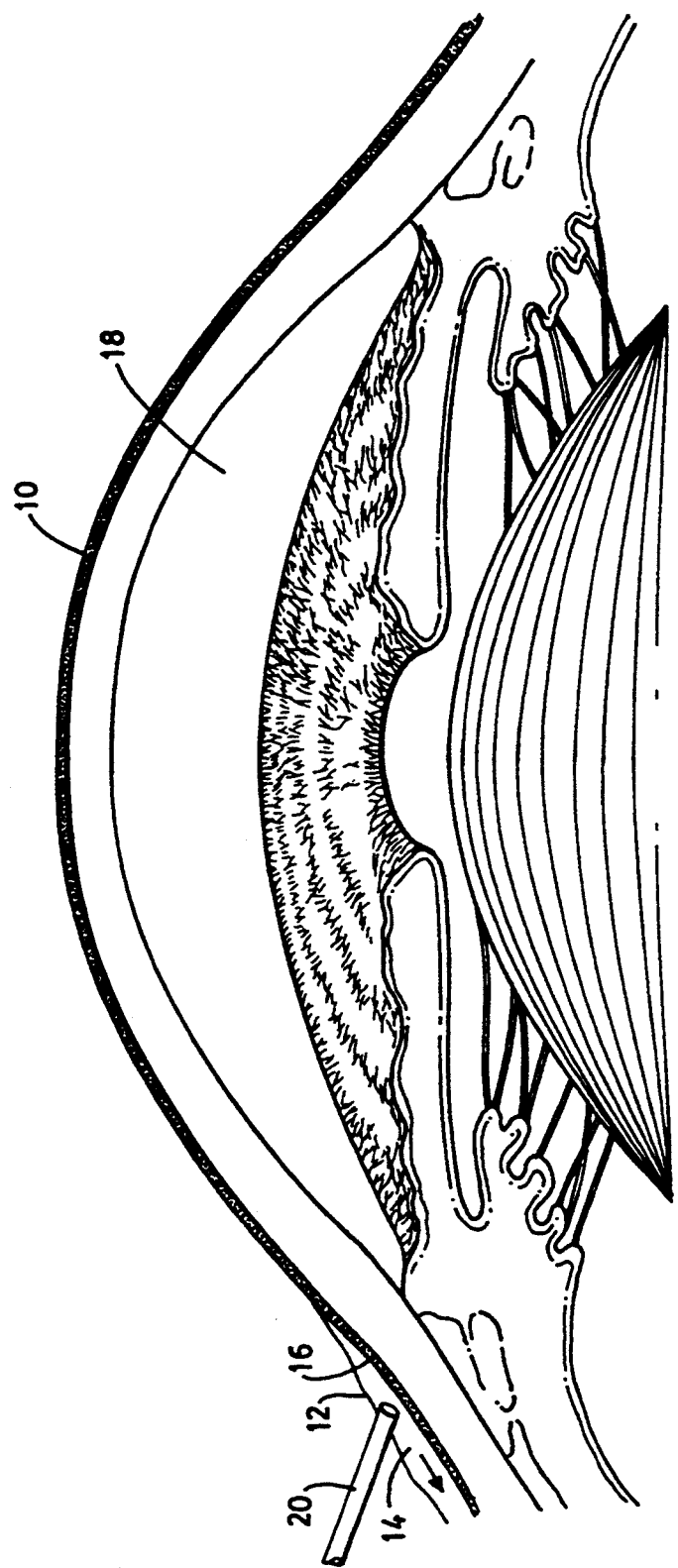
FIG. 2 illustrates the positioning of the needle into the subconjunctival space of the eye.

To create an alternative outflow channel, a fistula is made in the sclera 16. The first step in realizing the fistula is to insert a needle 20 through the conjunctiva 12 into the subconjunctival space 14 (see FIG. 2). The needle 20 should be of relatively small size. Preferably, a 26 gauge or a 27 gauge needle is utilized. Larger needles will leave a significant perforation of the conjunctiva 12 when the needle is removed upon completion of the procedure and thus, conjunctiva repair may be necessary to prevent fluid leakage. The needle tip 20 may be slightly curved. The needle is initially inserted as shown in FIG. 2.

Figure 3:
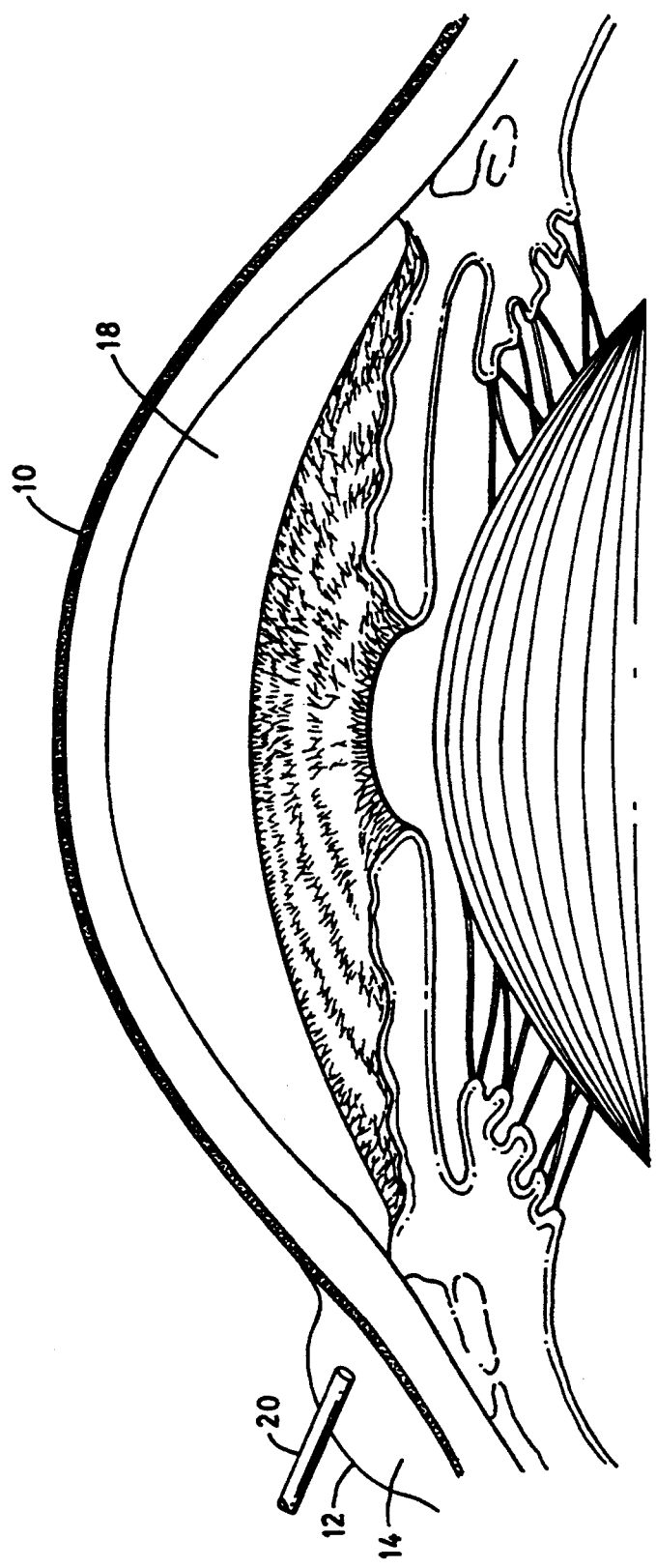
FIG. 3 depicts raising of the conjunctiva by infusing liquid through the needle.

Once the needle 20 is positioned properly inside the subconjunctival space 14, liquid is infused into the subconjunctival space 14. The liquid may be infused through the lumen of the needle 20. The infusion of the liquid brings about a raising of the conjunctiva 12 (FIG. 3). Suitable liquids for infusion include sodium hyaluronate sold under the brand names "HEALON" and "VISCOAT" sold by Pharmacia, Inc. and Alcon, respectively. These liquids have sufficient viscosity to prevent leakage of the liquid through the perforation created by the needle. The liquids used to raise the conjunctiva are gradually absorbed by the eye after completion of the procedure.

Once the conjunctiva is sufficiently raised, the needle 20 is moved to the target position near the corneoscleral junction known as the interior subconjunctiva. The infusion provides the added space and lubrication so that the movement to the target position is more readily achieved. An optical fiber 22 disposed within the needle 20 is then moved forward to the fistula site. This optical fiber 22 may be manually manipulated by the medical personnel performing the procedure so that the fiber 22 directly abuts the sclera. Positioning is achieved via a HeNe laser signal sent down the optical fiber 22. Since the conjunctiva 12 is translucent, the light from the HeNe laser illuminates the tip position.

Figure 4:
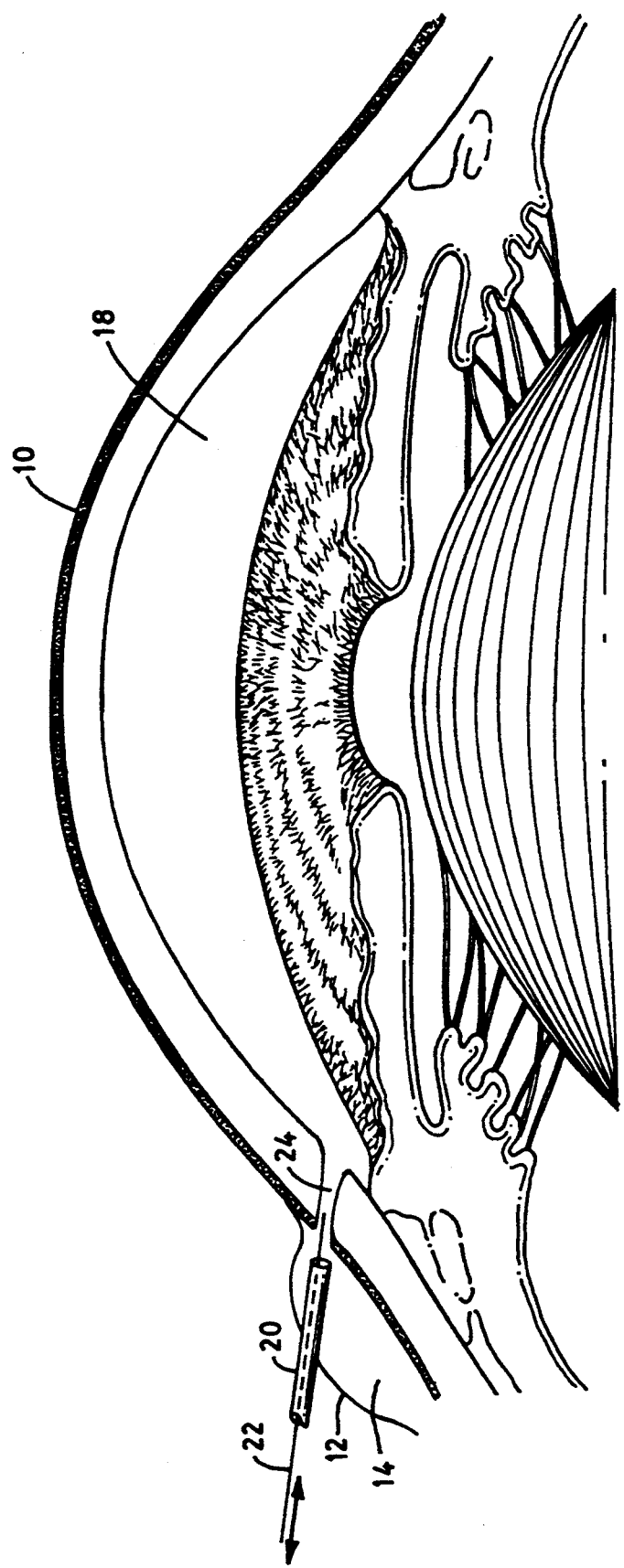
FIG. 4 shows creation of an outflow channel within the eye.

When the fiber 22 is in position, laser pulses from a higher power laser are sent down the optical fiber 22 to ablate the sclera 16 (FIG. 4). The ablation results in the creation of a fistula 24. As the fistula 24 is created, the optical fiber 22 is moved forward into the fistula 24 made in the sclera 16. Because the optical fiber 22 is moved forward in this manner, it is certain that the fiber 22 will be closely positioned against the target site, thus, maintaining ablating efficiency. Furthermore, by maintaining close proximity between the optical fiber 22 and the target, high irradiance of the tissue is maintained without absorbence by surrounding liquid. Lastly, this positioning enables laser wavelengths to be used that are not as deeply absorbed by the eye tissue as would otherwise be required. When the outflow channel has been completed, the optical fiber 22 and the needle 20 are removed from the conjunctiva 12.

Figure 5A:
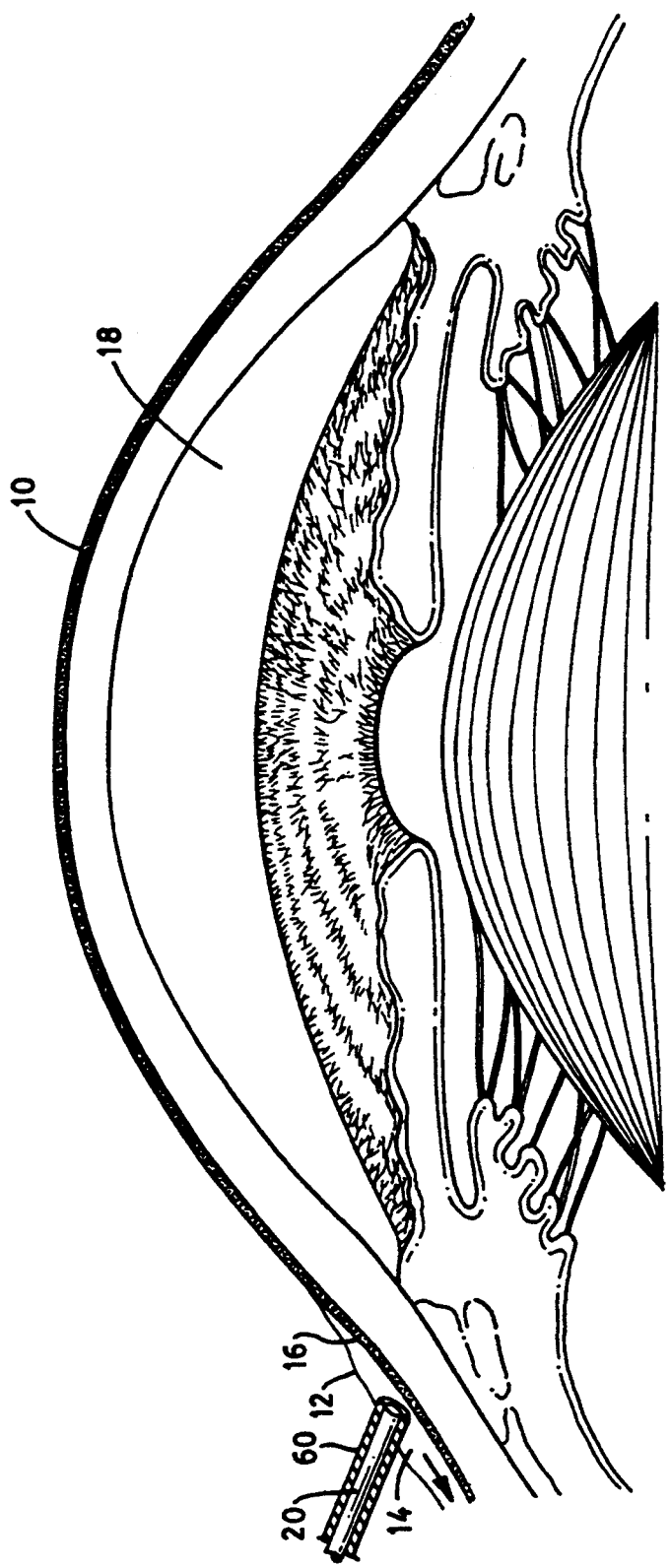
FIGS. 5a and 5b illustrate the use of a sheath that surrounds the needle to create a passageway into the subconjunctival space.
Figure 5B:
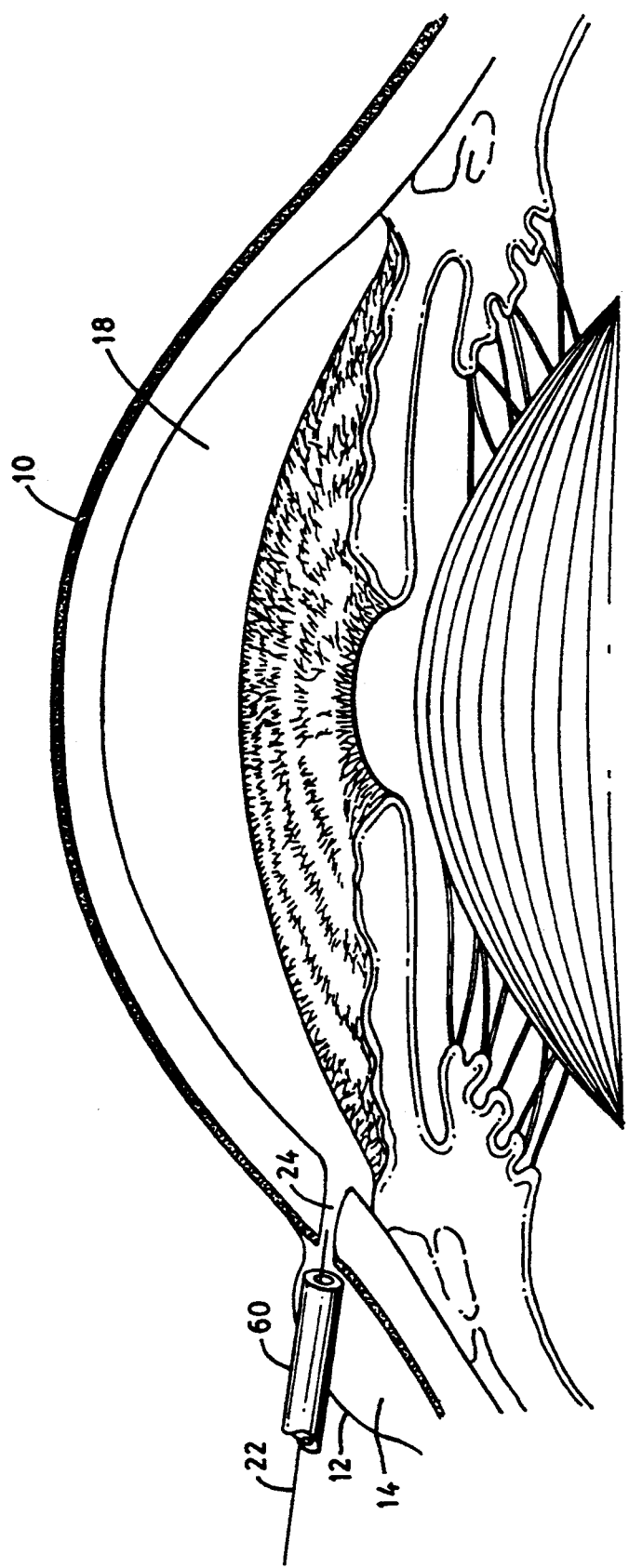

In accordance with an alternative embodiment, the needle 20 does not remain in the subconjunctival space 14 after the initial insertion through the conjunctiva 12. In the alternative embodiment, the needle 20 is covered by a sheath 60 as shown in FIG. 5a. The sheath 60 is preferably made of stainless steel. When the sheath 60 is employed, insertion occurs as previously described, except that both the sheath 60 and the needle 20 are inserted through the conjunctiva 12 into the subconjunctival space 14 (See FIG. 5a). Once the insertion is completed and the small bleb created, the needle 20 is removed while leaving the sheath 60 in place (FIG. 5b). The end of the sheath 60 in the subconjunctival space 14 is blunt to minimize trauma to tissue in the subconjunctival space 14. The sheath 60, thus, creates a passageway in which the optical fiber 22 may pass to the target area. The fiber 22 is then advanced to the corneo-scleral junction and is used as previously described to create a fistula 24.

Figure 6:
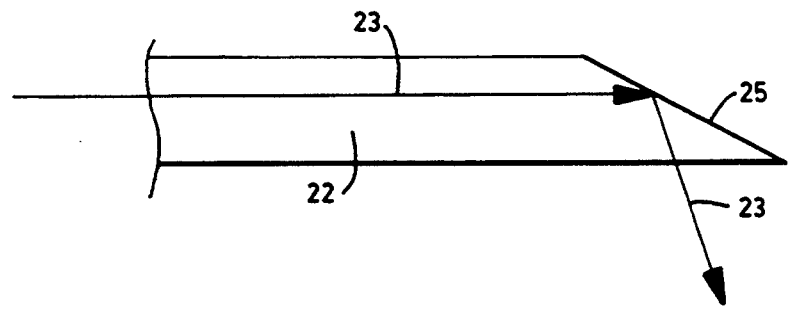
FIG. 6 depicts an optical fiber embodiment shaped like a needle to allow direct insertion of the fiber through the conjunctiva.

Yet another option is to make an incission in the conjunctiva with an optical fiber 22 shaped like a needle. An optical fiber with an outer diameter greater than 200 microns can be readily shaped like a needle. In particular, the optical fiber 22 has a sharp bevel tip 25 (FIG. 6) that can cut through the conjunctiva 12 (FIG. 1). The fiber 22 still, nevertheless, serves as a means for delivering laser energy to create a fistula 24. The bevel face 25 is coated to provide reflection of laser energy in the middle infra-red range. Reflection of the laser beam may also be realized by using a high index refraction material at the tip 25 such as diamond or sapphire. The laser beam 23 reflects off the bevel tip 25 as shown in FIG. 6. The fiber 22 is used like its counterparts previously discussed to create a fistula.

Figure 7:
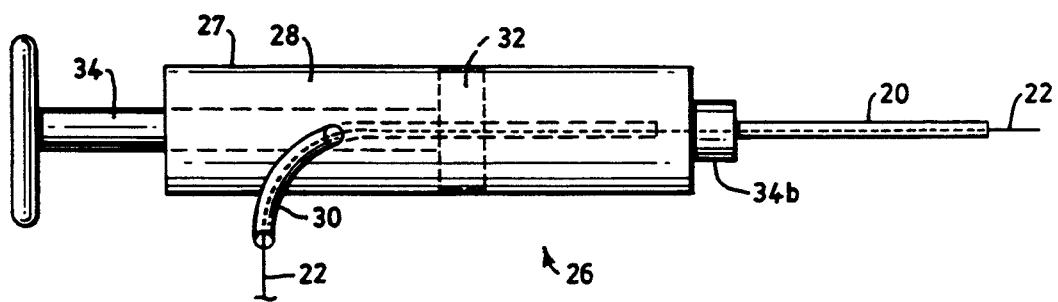
FIG. 7 shows a first syringe embodiment having a channel for carrying an optical fiber that enters from the side of the syringe.

An apparatus for performing the above described procedure is shown in FIG. 7. The apparatus 26 is comprised primarily of a syringe 27 and a needle 20. The syringe 27 has a first channel 28 for infusing liquids and a second channel 30 that enters the first channel via the side to run through the center of the first channel 28. The second channel 30 is used as a passageway by the optical fiber 22. The syringe 27 also includes a plunger 34 having a rubber stopper 32 attached to the end of it. The plunger 34 is used to infuse liquids through the needle 20. The needle 20 also serves the additional role of carrying the optical fiber 22. As such, the inner lumen of the needle 20 is shared by the optical fiber 22 and liquids that are infused via the plunger 34. A hole is provided in the stopper 32 for the second channel 30 to pass. The syringe 27 portion of the apparatus and the needle 20 are connected by a standard lure connector 34.

Figure 8:
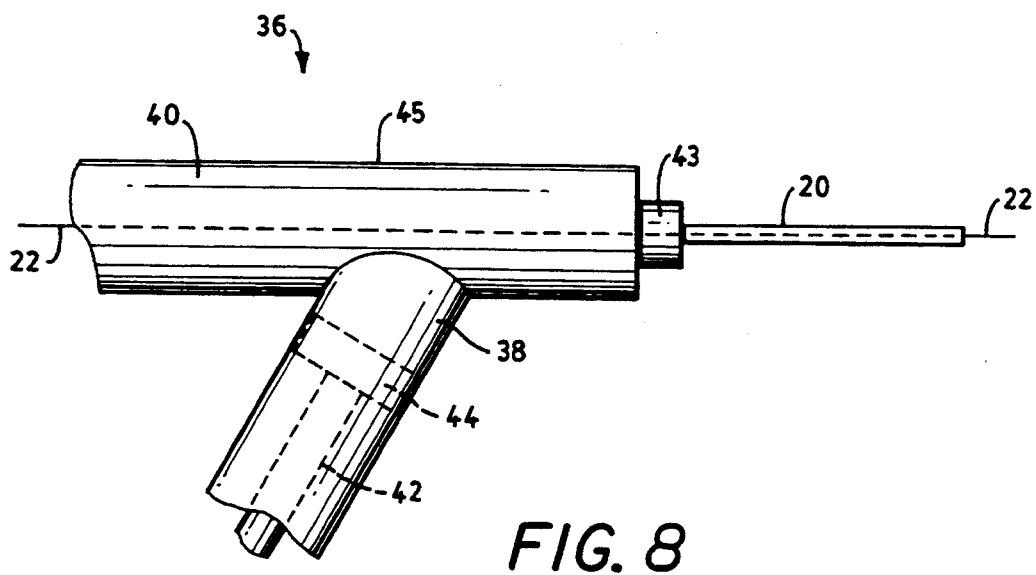
FIG. 8 depicts a second syringe embodiment having a channel for infusing liquids that enters the syringe via the side of the syringe.

The second embodiment of the invention is shown in FIG. 8. This embodiment 36 is, likewise, comprised of a syringe 45 and a needle 20. The syringe, however, is composed primarily of the central channel 40 through which the optical fiber 22 travels and a secondary merging side channel 38 through which liquid is infused. Like the embodiment depicted in FIG. 7, this embodiment includes a plunger 42 with a rubber stopper 44. Similarly, a hole must be provided in the stopper 44 for the optical fiber 22 to travel. A lure connector 43 connects the syringe 45 with the needle 20. The primary difference between this embodiment, and the previously described embodiment is the different respective channel positions.

Figure 9:
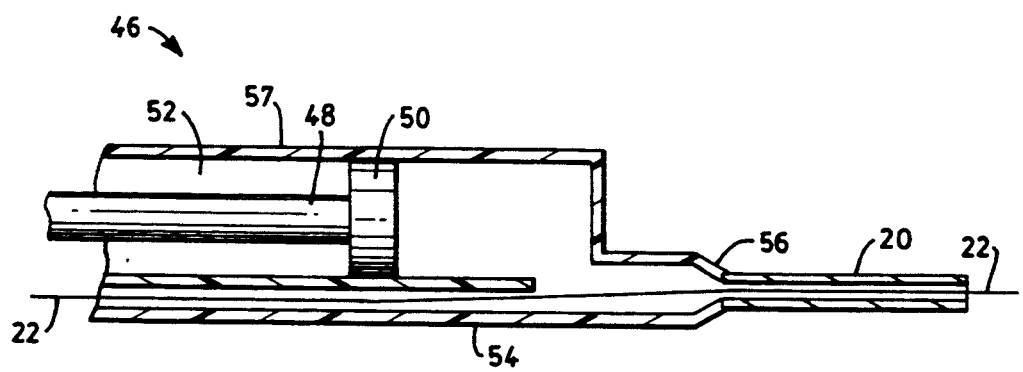
FIG. 9 illustrates a third syringe embodiment wherein the channel for the-optical fiber runs parallel along the side of the syringe to the channel for infusing liquids.

A third embodiment is depicted in FIG. 9. The third embodiment 46 is also a syringe 57 and a needle 20. In this embodiment, instead of one channel merging into the other channel, the two channels 52 and 54 are kept separate. The upper channel 52 is used for infusing liquids. It includes a plunger 48 and stopper 50. The lower channel 54 is used for carrying the optical fiber 22. The syringe 57 is connected to the needle via a lure connector 56.

All three of the above described embodiments shown in FIGS. 7, 8 and 9, respectively, may be utilized with the sheath 60 previously described. Moreover, all three embodiments provide for manipulation of the optical fiber 22 independent of the syringe portion of the apparatus. Furthermore, these three embodiments allow a single apparatus to infuse liquid into the subconjunctival space 14 as well as to carry an optical fiber for ablating the sclera.

The above described embodiments provide several benefits over techniques known in the prior art. To understand more fully one of the primary benefits, it is best to examine the absorption curve of water depicted in FIG. 10. The absorption of laser light by the water in tissue is what brings about the thermal cutting effect of the laser. As can be seen in the plot of FIG. 10, absorption is quite high in the infrared range. Such wavelengths may not be used in prior art embodiments because of the necessity of passing the laser beam through the cornea. In the visible wavelengths suited to the cornea, absorption is low, so in prior procedures methylene blue dye, which has its primary absorption in the neighborhood of 0.660 to 0.666 microns, has been used. The present invention, in contrast, delivers the laser beam directly to the sclera through a fiber and thus allows for the use of laser light having wavelengths in the infrared. It is preferred that the laser radiation have a wavelength greater than 1.5 microns. The graph shown in FIG. 9 reveals that at these wavelengths water has an absorption coefficient of greater than 1 $cm^{-1}$. At wavelengths greater than 2.0 microns a coefficient of absorption of greater than 10 $cm^{-1}$ is found. However, at wavelengths greater than 3.0 microns, transmission of the light through the fiber is difficult. Even at 2.9 microns, a short fiber and an articulated arm is required.

Suitable laser sources for generating such wavelengths of laser radiation include lasers that employ a yttrium aluminum garnet host crystal (i.e. YAG lasers). The most promising of the YAG lasers include the erbium:YAG (2.9 microns), the homium:YAG (2.1 microns) and the thulium:YAG (2.0 microns). These lasers provide laser radiation in the appropriate range of wavelengths.

A short pulse duration minimizes damage to surrounding tissue, but the duration must be sufficiently long to permit transmission of sufficient energy per pulse to ablate the tissue. A range of 10 to 225 microseconds is preferred.

The preferred laser is the thulium:YAG laser having a wavelength 2.0 microns a repetition rate of 2 to 5 pulses per second delivering about 100 millijoules per pulse through a 100 to 200 micron fiber.

While the invention has been particularly shown and described with reference to preferred embodiments thereof, it will be understood by those skilled in the art that various changes in form and detail may be made without departing from the spirit and scope of the invention as described in the appended claims. For instance, syringe configurations different than those described may be equally suitable. Furthermore, it may not be necessary to raise the conjunctiva with liquid before ablation.

I claim:

1. An ab externo method of sclerostomy, comprising the steps of:
   a) creating an opening to a subconjunctival space between a conjunctiva and a sclera o an eye and positioning in said opening a generally tubular member such that said tubular member maintains said opening to said subconjunctival space;
   b) subsequently positioning an optical fiber for carrying laser radiation through said tubular member into the subconjunctival space such that the optical fiber is closely positioned relative to the sclera; and
   c) ablating the sclera of the eye with laser radiation carried by the optical fiber to create a fistula in the sclera and moving the optical fiber into the fistula while further ablating the sclera with laser radiation to create an outflow channel to decrease intraocular pressure in the eye.

2. A method as recited in claim 1 wherein the ablating step comprises ablating with laser radiation having a wavelength in the range of 1.5 to 3.0 microns.

3. A method is recited in claim 1 wherein ablating step comprises ablating with pulses of laser radiation having a duration in the range of 10 to 225 microseconds per pulse.

4. A method as recited in claim 1 wherein the ablating step comprises ablating with pulses of laser radiation in the range of 50 to 200 millijoules per pulse.

5. A method as recited in claim 1 wherein the ablating step comprises moving the optical fiber and the tubular member relative to one another.

6. A method as recited in claim 1 wherein the ablating step comprises advancing the optical fiber into the fistula so that the optical fiber abuts a region of the sclera being ablated.

7. A method as recited in claim 1 further comprising the step of raising a conjunctiva by infusing liquid into the subconjunctival space.

8. A method as recited in claim 7 wherein the step of creating an opening includes creating said opening with a needle having a lumen, and infusing said liquid through said lumen.

9. An ab externo method of sclerostomy, comprising the steps of:
   a) creating an opening to a subconjunctival space between a conjunctiva and a sclera of an eye and positioning in said opening a generally tubular member such that said tubular member maintains said opening to said subconjunctival space;
   b) subsequently passing an optical fiber for carrying laser radiation through said member into the subconjunctival space such that the optical fiber is closely positioned relative to the sclera; and
   c) ablating the sclera with laser radiation carried by the optical fiber to create a fistula in the sclera and moving the optical fiber into the fistula while further ablating the sclera with laser radiation to create an outflow channel to decrease intraocular pressure in the eye.

10. A method as recited in claim 9 wherein said creating step comprises creating an opening, and positioning in said opening a needle that is inserted through the conjunctiva.

11. A method as recited in claim 9 wherein the creating step comprises forming an incision created by the generally tubular member in the conjunctiva.

12. A method as recited in claim 9 wherein the creating step comprises forming an incision in the conjunctiva created by the optical fiber which is shaped like a needle.

13. A method as recited in claim 9 wherein the passing step comprises manually passing the optical fiber through the opening.

14. A method as recited in claim 9 further comprising the step of raising a conjunctiva by infusing liquid in to the subconjunctival space.

15. A method as recited in claim 9 wherein the ablating step comprises advancing the optical fiber into the fistula so that the optical fiber directly abuts a region of the sclera to be ablated.

16. A method as recited in claim 9 wherein the ablating step comprises sending initial pulses of laser radiation to create a fistula site in the sclera and, then, moving the optical fiber into the fistula site for further ablation.

17. A method as recited in claim 9 wherein the ablating step comprises ablating with laser radiation having a wavelength in the range of 1.5 to 3.0 microns.

18. A method is recited in claim 9 wherein ablating step comprises ablating with pulses of laser radiation having a duration in the range of 10 to 225 microseconds per pulse.

19. A method as recited in claim 9 wherein the ablating step further comprises moving the optical fiber and the tubular member relative to one another.

20. An ab externo method for treating glaucoma in an eye having a conjunctiva and sclera, comprising the steps of:

a) inserting a needle through the conjunctiva of the eye, said needle being surrounded by a sheath;

b) removing the needle from the conjunctiva but leaving the sheath to provide a passage through the conjunctiva;

c) subsequently passing an optical fiber for carrying laser radiation through the passage into a subconjunctival space between the conjunctiva and the sclera such that the fiber is closely positioned relative to the sclera; and d) ablating the sclera of the eye with laser radiation from the optical fiber to create a fistula in the sclera and moving the optical fiber into the fistula while further ablating the sclera with laser radiation to create an outflow channel to decrease intraocular pressure in the eye.

21. A method as recited in claim 20 further comprising the step of raising the conjunctiva by infusing fluid into the subconjunctival space.

22. A method as recited in claim 20 wherein the ablating step comprises ablating with laser radiation having a wavelength in the range of 1.5 to 3.0 microns.

23. A method as recited in claim 20 wherein the ablating step comprises ablating with pulses of laser radiation having a duration in the range of 10 to 225 microseconds per pulse.

24. A method as recited in claim 20 wherein the ablating step comprises ablating with pulses of laser radiation from the optical fiber in the range of 50 to 200 millijoules per pulse.

25. A method as recited in claim 20 wherein the ablating step comprises sending pulses of laser radiation to create a fistula in the sclera and subsequently, moving the optical fiber into the fistula for further ablating.

26. A method as recited in claims 20 wherein the ablating step comprises advancing the optical fiber into the fistula so that the optical fiber abuts a region of the sclera to be ablated.

* * * * *